(12) United States Patent
Dewis et al.

(10) Patent No.: US 7,361,376 B2
(45) Date of Patent: Apr. 22, 2008

(54) ALKYLDIENAMIDES EXHIBITING TASTE AND SENSORY EFFECT IN FLAVOR COMPOSITIONS

(75) Inventors: Mark L. Dewis, Matawan, NJ (US); Michelle E. Huber, River Vale, NJ (US); Michael V. Cossette, Plainsboro, NJ (US); David O. Agyemang, Sayreville, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 800 days.

(21) Appl. No.: 10/411,672

(22) Filed: Apr. 11, 2003

(65) Prior Publication Data

US 2004/0202760 A1    Oct. 14, 2004

(51) Int. Cl.
*A23L 1/22* (2006.01)
(52) U.S. Cl. .......... 426/534; 426/650; 554/35; 554/69
(58) Field of Classification Search .......... 426/534, 426/536, 537, 538, 650; 554/35, 69
See application file for complete search history.

(56) References Cited

U.S. PATENT DOCUMENTS

| | | | |
|---|---|---|---|
| 3,111,127 A | 11/1963 | Jarboe | |
| 4,029,759 A | 6/1977 | Humbert et al. | |
| 4,032,661 A | 6/1977 | Rowsell et al. | |
| 4,150,052 A | 4/1979 | Watson et al. | |
| 4,153,679 A | 5/1979 | Rowsell et al. | |
| 4,185,106 A | 1/1980 | Dittmar et al. | |
| 4,226,988 A | 10/1980 | Watson et al. | |
| 4,296,093 A | 10/1981 | Rowsell et al. | |
| 4,470,982 A | 9/1984 | Winkler | |
| 4,472,421 A | 9/1984 | Buchel et al. | |
| 5,009,893 A | 4/1991 | Cherukuri et al. | |
| 5,288,510 A | 2/1994 | Gregory et al. | |
| 5,494,675 A | 2/1996 | Beilharz et al. | |
| 5,545,424 A | 8/1996 | Nakatsu et al. | |
| 5,624,666 A | 4/1997 | Coffindaffer et al. | |
| 5,641,480 A | 6/1997 | Vermeer | |
| 5,725,865 A | 3/1998 | Mane et al. | |
| 5,730,965 A | 3/1998 | Rapaport | |
| 5,843,466 A | 12/1998 | Mane et al. | |
| 5,955,066 A | 9/1999 | Sako et al. | |
| 6,096,324 A | 8/2000 | Mansouri | |
| 6,110,520 A | 8/2000 | He et al. | |
| 6,200,554 B1 | 3/2001 | Yeoh et al. | |
| 6,210,695 B1 | 4/2001 | Beerse et al. | |
| 6,248,315 B1 | 6/2001 | Young et al. | |
| 6,251,463 B1 | 6/2001 | Rossy et al. | |
| 6,294,186 B1 | 9/2001 | Beerse et al. | |
| 6,297,203 B1 | 10/2001 | Guskey et al. | |
| 6,299,900 B1 | 10/2001 | Reed et al. | |
| 6,303,817 B1 | 10/2001 | Boden et al. | |
| PP12,213 P2 | 11/2001 | Zimmermann | |
| 6,328,982 B1 | 12/2001 | Shiroyama et al. | |
| 6,333,180 B1 | 12/2001 | Farbood et al. | |
| 6,338,855 B1 | 1/2002 | Albacarys et al. | |
| 6,365,215 B1 | 4/2002 | Grainger et al. | |
| 6,365,601 B1 | 4/2002 | Gaikar et al. | |
| 6,391,886 B1 | 5/2002 | Lee | |
| 6,451,844 B1 | 9/2002 | Watkins et al. | |
| 6,455,080 B1 | 9/2002 | Wolf et al. | |
| 6,541,050 B1 | 4/2003 | Bonorden et al. | |

(Continued)

FOREIGN PATENT DOCUMENTS

EP    1 121 927 A2    2/2001

(Continued)

OTHER PUBLICATIONS

U.S. Appl. No. 10/411,672, filed Apr. 11, 2003, Pending; No OA received.

(Continued)

*Primary Examiner*—Leslie Wong
(74) *Attorney, Agent, or Firm*—Elizabeth M. Quirk; Xu Fan Tseng; Joseph F. Leighter

(57) ABSTRACT

Alkyldienamides compounds suitable for use as flavoring agents are disclosed. The compounds are used as flavors since they possess umami characteristics or other desirable organoleptic properties. The disclosed compounds are defined by the structure set forth below:

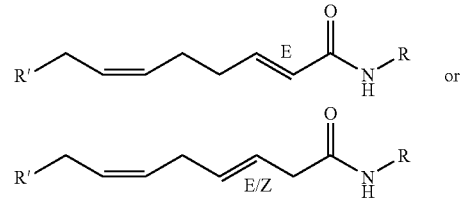

wherein R is methyl, ethyl, n-propyl, isopropyl, cyclopropyl, n-butyl, sec-butyl, isobutyl, cyclobutyl, $CH_2CH(CH_3)CH_2CH_3$, $CH_2CH(OH)CH_3$, $CH(CH_3)CH_2OH$, $CH_2C(CH_3)_2OH$, $CH_2CH_2OH$,

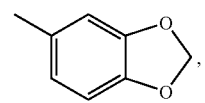

cyclopentyl or allyl; and wherein R' is methyl, ethyl, n-propyl, n-butyl or n-pentyl, n-hexyl.

6 Claims, No Drawings

U.S. PATENT DOCUMENTS

| | | | |
|---|---|---|---|
| 6,544,499 B1 | 4/2003 | Glenn, Jr. et al. |
| 6,572,914 B1 | 6/2003 | Borlinghaus |
| 6,576,224 B1 | 6/2003 | Osbakken et al. |
| 6,576,225 B1 | 6/2003 | Kilcher et al. |
| 6,576,228 B1 | 6/2003 | Crookham et al. |
| 6,579,513 B1 | 6/2003 | Tashjian et al. |
| 6,579,514 B1 | 6/2003 | Hall et al. |
| 6,579,516 B1 | 6/2003 | Mansouri |
| 6,579,535 B2 | 6/2003 | Valentine et al. |
| 6,579,543 B1 | 6/2003 | McClung |
| 2001/0032645 A1 | 10/2001 | Cronk et al. |
| 2001/0043912 A1 | 11/2001 | Michael |
| 2002/0012640 A1 | 1/2002 | Mohammadi et al. |
| 2002/0039591 A1 | 4/2002 | Dahle |
| 2002/0122778 A1 | 9/2002 | Wolfson |
| 2002/0142015 A1 | 10/2002 | Kumamoto et al. |
| 2002/0173436 A1 | 11/2002 | Sonnenberg et al. |
| 2003/0035784 A1 | 2/2003 | Inoue et al. |
| 2003/0068330 A1 | 4/2003 | Goto et al. |
| 2003/0072842 A1 | 4/2003 | Johnson et al. |
| 2003/0082124 A1 | 5/2003 | Hammer |
| 2003/0082129 A1 | 5/2003 | Buckingham et al. |
| 2003/0082271 A1 | 5/2003 | Wolf et al. |
| 2003/0091721 A1 | 5/2003 | Ohta et al. |
| 2003/0095936 A1 | 5/2003 | Light |
| 2003/0095938 A1 | 5/2003 | Casero |
| 2003/0113357 A1 | 6/2003 | Bell et al. |
| 2003/0152682 A1 | 8/2003 | Ley et al. |
| 2004/0241312 A1 | 12/2004 | Gatfield et al. |

FOREIGN PATENT DOCUMENTS

| | | |
|---|---|---|
| EP | 1 121 927 A2 | 8/2001 |
| EP | 1 122 233 A1 | 8/2001 |
| GB | 1 438 205 | 3/1976 |
| JP | 04 803546 | 12/1970 |
| JP | 56087505 | 7/1981 |
| WO | WO 93/23005 | 11/1993 |
| WO | WO 98/07404 | 2/1998 |
| WO | WO 99/07235 | 2/1999 |
| WO | WO 00/45815 | 8/2000 |
| WO | WO 02/51392 | 4/2002 |
| WO | WO 2004/000787 A2 | 12/2003 |
| WO | WO 2004/011415 | 2/2004 |
| WO | WO 2004/043906 | 5/2004 |

OTHER PUBLICATIONS

U.S. Appl. No. 10/783,652, filed Feb. 20, 2004, Pending; No OA received.

U.S. Appl. No. 10/611,025, filed Jul. 1, 2003, Pending; No OA received.

U.S. Appl. No. 10/618,367, filed Jul. 10, 2003, Allowed; Petition to withdraw from issue submitted.

U.S. Appl. No. 10/861,751, filed Jun. 4, 2004, Pending; No OA received.

U.S. Appl. No. 10/678,558, filed Oct. 3, 2003, Pending; No OA received.

U.S. Appl. No. 10/919,631, filed Aug. 17, 2004, Pending; No OA received.

U.S. Appl. No. 10/939,096, filed Sep. 10, 2004, Pending; No OA received.

Prior Art Submission Under CFR 1.291 , no date.

"Systematic Studies on Structure and Physiological activity of Cyclic α-Keto Enamines, a Novel Class of 'Cooling' Compounds", J.Agric.Food Chem. 2001, 49, 5383-5390.

U.S. Appl. No. 10/643,542, filed Aug. 19, 2003, Flamer et al.

Search for Unsaturated Decanoic Acid Compounds, no date.

ACS Symposium Series 867, Challenges in Taste Chemistry and Biology, Sponsored by the ACS Division of Agricultural and Food Chemistry, Chapter 9, Pungent and Tingling Compounds in Asian Cuisine, Galopin et al, pp. 139-152, no date.

English abstract of Saureamide In Hochruckextrakten Aus Muntokpfeffer in English. H. Kollmannsberger und S. Nitz, Chem. Mikrobiol. Technol. Lebensm. 14, 87-94 (1992).

"Pellitorine Isomers. II. The Synthesis of N-Isobutyl-trans-2, trans-4-decadienamide[1,2,3]", Martine Jacobson, vol. 75, Jun. 5, 1953, pp. 2584-2586.

"Alkamides from Artemisia dracunculus", Bouchra Saadali et al., Phytochemistry , Pergamon Press, vol. 58, No. 7, Dec. 2001, pp. 1083-1086.

"Isobutylamide numbing agents of toothache grass, Ctenium aromaticum" Rubi Gamboa-Leon et al., Biochemical Systematics and ecology, vol. 28, 2000, pp. 1019-1021.

GRAS Flavoring Substances 20, Food Technology, vol. 55, No. 12, Dec. 2001 at p. 53.

Rule, et al, Optical Activity and the Polarity of Substituent Groups Part VIII. Growing-chain Effects and the Ortho-Effect in Benzoic Esters, J.Chem.Soc. 1928 (Part I), pp. 1347-1361.

SciFinder (Nov. 20, 2002; Trademark of Chemical Abstracts Service), to wit: malonamic acid, p-menth-3-yl ester, ±-(8Cl) having CAS Registry No. 6129-88-0.

Jaloner, et al, A Molecular Approach to Flavor Synthesis. I. Menthol Esters of Varying Size and Polarity, Journal of Polymer Science:Polymer Chemistry Edition, vol. 18, 2933-2940 (1980).

Rameswak, et al, Bioactive N-isobutylamides from flower buds of *Spilanthes acmella*, Phytochemistry 51, (1999), 729-732.

Snider, et al, Synthesis of the N-(1E)-Alkenyl)-2Z, 4Z)-heptadienamide Side Chain of Salicylihalamide A and Apicularens A and B, Organic Letters (2000), vol. 2, No. 3, pp. 407-408.

Purber, et al, Stereospecific diene Synthesis using Acetylene Carbocupration; Preparation of Novel Orangeworm Pheremone and Leukotriene Analogues, J.Chem.Soc.Perkin Trans. I, 1986, pp. 1809-1815.

U.S. Appl. No. 10/411,672, filed Apr. 11, 2003, Dewis et al.

U.S. Appl. No. 10/643,542, filed Aug. 19, 2003, Flammer et al.

U.S. Appl. No. 10/611,025, filed Jul. 1, 2003, Dewis et al.

"Pungent Alkamides from Spilantes Acmella L. Var. Oleracea Clarke," Nakatani N et al. Bioscience Biotechnology Biochemistry, Japan Soc. For Bioscience Biotechnology and Agrochem., vol. 56, No. 5, 1992, pp. 759-762.

Databse Beilstein, Beilstein Institute for Organic Chemistry, J. Chem. Soc., 1952, p. 4338.

"Amides of vegetable origin. VII. Synthesis of N-isobutyldodeca-trans-2, trans-4, trans-8-ans trans-2, trans-4, cis-8-trienamide and the relation to Sanshool I," Crombie L. et al., Journal of Chemical Society, Abstracts, pp. 4244-4249, 1955.

"Isobutylamide numbing agents of toothache grass, Ctenium aromaticum," Rubi Gamboa-Leon et al., Biochemical Systematics and Ecology, 28(10), 2000, pp. 1019-1021.

"Structure and synthesis of a new hypotensive vasodilator isolated from *Spreptomyces aerofaciens*," Tanaka, Hirokazu et al., Tetrahedron Letters 22(35), 1981, pp. 3421-3422.

"The Synthesis of Long-Chain Aliphatic Acids from Acetylenic Compounds. Part V. The Synthesis of trans-cis-Herculin, Part IV," 1950, pp. 2693-2695.

ALKYLDIENAMIDES EXHIBITING TASTE AND SENSORY EFFECT IN FLAVOR COMPOSITIONS

FIELD OF THE INVENTION

Alkamide compounds having umami taste and somatosensory attributes in the oral cavity.

BACKGROUND OF THE INVENTION

The term Umami, from the Japanese word to describe savory or meaty, is the term used to describe the unique overall fullness, savory or salivatory taste of food. Materials that exhibit this taste quality generally potentiate the intensity of glutamate solutions and this is one important characteristic of umami taste. It is increasingly becoming recognized as the fifth sense of taste, the others being sour, sweet, salt and bitter. Compounds traditionally described as possessing this character are monosodium glutamate (MSG), protein hydrolysates, some amino acids and certain nucleotides and phosphates.

MSG is the most widely used material as a 'taste enhancer' where it synergizes the perception of 'savory' ingredients, but has also been alleged to cause allergic reaction to a proportion of the population. Since MSG is widely used in Asian cuisine, especially Chinese, this has been referred to as the Chinese Restaurant Syndrome. Free glutamic acid occurs in food but this also is the subject of review by The Federation of American Society for Experimental Biology.

Among other chemical compounds several nucleotides have also been described to exhibit the umami effect Adenosine 5'-(trihydrogen diphosphate), 5'-Cytidylic acid (5'-CMP), 5'-Uridylic acid (5'-UMP), 5'-Adenylic acid (5'-AMP), 5'-Guanylic acid (5'-GMP), 5'-Inosinic acid (5'-IMP) and the di-sodium salts of 5'-Guanylic acid and 5'-Inosinic acid.

Recent literature cites an extensive range of other organic compounds as taste active components of mixtures shown to give the umami taste effect. These include but are not necessarily limited to: organic acids such as succinic acid, lactic acid, saturated straight chain aliphatic acids of six, eight, fourteen, fifteen, sixteen, and seventeen carbon chain lengths, Z4,Z7, Z10,Z13,Z16,Z19-docosahexaenoic acid, Z5,Z8,Z11,Z14,Z17-eicosapentaenoic acid, Z9,Z12, Z16, Z19-octadecadienoic acid, Z9-octadecenoic acid, glutaric acid, adipic acid, suberic acid, and malonic acid. Aminoacids having umami effects reported in the literature include glutamic acid, aspartic acid, threonine, alanine, valine, histidine, proline tyrosine, cystine, methionine, pyroglutamic acid, leucine, lycine, and glycine. Dipeptides possessing umumi properties include Val-Glu and Glu-Asp.

Other miscellaneous compounds having umami properties include alpha-amino adipic acid, malic acid, alpha-aminobutyric acid, alpha-aminoisobutyric acid, E2,E4-hexadienal, E2,E4-heptadienal,E2,E4-octadienal, E2,E4-decadienal, Z4-heptenal, E2,Z6-nonadienal, methional, E3,E5-octadien-2-one, 1,6-hexanediamine, tetramethylpyrazine, trimethylpyrazine, cis-6-dodecen-4-olide and a number of naturally occurring amino-acids.

The discovery of alkyldienamides in a wide variety of botanicals and the use of some of these to impart flavor and/or a sensation is the subject of a huge amount of literature. Molecules of this type have also been found to exhibit biological activity, most notably anti-bacterial, anti-fungal and insecticidal activity. The most significant compounds in this class, provided with their Chemical Abstract Service number in brackets are: hydroxy-alpha-sanshool [83883-10-7], alpha-sanshool [504-97-2], hydroxy-epislon-sanshool [252193-26-3], gamma-sanshool [78886-65-4], spilanthol [25394-57-4], N-isobutyl E2, E4, 8, 11-dodecatetraenamide[117824-00-7 and 310461-34-8], isoaffinin [52657-13-3], pellitorine [18836-52-7] and bunganool [117568-40-8] along with a small number of geometrical isomers thereof.

Despite these disclosures there is an ongoing need for new flavor ingredients particularly those that exhibit advantageous organoleptic properties.

SUMMARY OF THE INVENTION

Our invention relates to novel compounds and a process for augmenting or imparting a taste or somatosensory effect to a foodstuff, chewing gum, medicinal product, toothpaste, alcoholic beverage, aqueous beverage or soup comprising the step of adding to a foodstuff, chewing gum, medicinal product, toothpaste, alcoholic beverage, aqueous beverage or soup a taste or sensation augmenting, enhancing or imparting quantity and concentration of at least one N-substituted unsaturated aliphatic alkyl amide defined according to the structure:

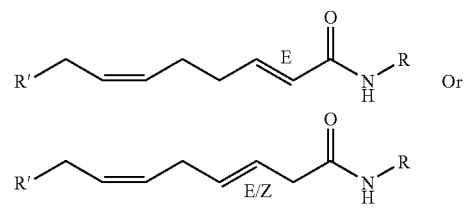

Formula I wherein R is methyl, ethyl, n-propyl, isopropyl, cyclopropyl, n-butyl, sec-butyl, isobutyl, cyclobutyl, $CH_2CH(CH_3)$ $CH_2CH_3$, $CH_2CH(OH)CH_3$, $CH(CH_3)CH_2OH$, $CH_2C(CH_3)_2OH$, $CH_2CH_2OH$,

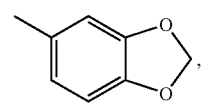

cyclopentyl or allyl; and wherein R' is methyl, ethyl, n-propyl, n-butyl or n-pentyl and n-hexyl. As used herein these compounds will be referred to hereinafter as "alkyldienamides".

DETAILED DESCRIPTION OF THE INVENTION

Our invention specifically relates to the novel compositions according to the Formula I above, which have been described as having the following flavor characteristics,

| R | R' | Compound | Primary characteristic | Secondary characteristic |
|---|---|---|---|---|
| CH$_2$CH$_2$OH | n-butyl | N-(2-Hydroxyethyl)E2, Z6-dodecadienamide | Tingle, melon flavor | Pepper like warmth |
| CH$_2$CH(CH$_3$)CH$_2$CH$_3$ | n-butyl | N-(2-methylbutyl)E2, Z6-dodecadienamide | Fruity | Salt like |
| 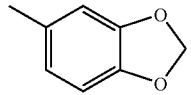 | Me | N-(3,4-methylenedioxy)benzyl E2, Z6-nonadienamide | Numbing | Tingle |
| CH$_2$CH(CH$_3$)CH$_2$CH$_3$ | Me | N-(2-methylbutyl)E2, Z6-nonadienamide | Bitter | Tingle |
| cyclopropyl | n-butyl | N-Cyclopropyl E2, Z6-dodecadienamide | Fatty mouthfeel | Wasabi type burn |
| cyclopropyl | Me | N-Cyclopropyl E2, Z6-nonadienamide | Unami | Enhancement |
| ethyl | n-butyl | N-Ethyl E2, Z6-dodecadienamide | MSG like | Burning |
| ethyl | Me | N-Ethyl E2, Z6-nonadienamide | Umami | Enhancement |
| isobutyl | n-butyl | N-Isobutyl E2, Z6-dodecadienamide | Numbing | Tingle |
| isobutyl | Me | N-Isobutyl E2, Z6-nonadienamide | Tingle/numbing | MSG like |
| isopropyl | n-butyl | N-Isopropyl E2, Z6-dodecadienamide | Melon/cucumber Flavor | Tingle |
| isopropyl | Me | N-Isopropyl E2, Z6-nonadienamide | Cucumber taste | Tingle |
| Me | Me | N-Methyl E2, Z6-nonadienamide | Tingle | Numbing | and uses thereof in augmenting or imparting an olfactory effect or sensation such as a taste or somatosensory effect to a foodstuff, chewing gum, medicinal product, toothpaste, alcoholic beverage, aqueous beverage or soup particularly providing a (a) umami taste, (b) tingle sensation, (c) warming/burning sensation, (d) numbing sensation, (e) cooling sensation and (f) salt effects.

More specifically, examples of the organoleptic properties for the alkyldienamides of our invention are as follows:

| Compound | Taste and flavor characteristics |
|---|---|
| N-(2-Hydroxypropyl) E2, Z6-nonadienamide | Cloying, fatty, cod liver oil, fishy. |
| N-(2-Hydroxyethyl) E2, Z6-dodecadienamide | Strong melon flavor, tingle, burn, pepper taste. |
| N-(2-methylbutyl) E2, Z6-dodecadienamide | Slightly fruity, tingle, salty. |
| N-(3,4-methylenedioxy) benzyl E2, Z6-nonadienamide | Numbing and tingle. |
| N-(2-methylbutyl) E2, Z6-nonadienamide | Metallic, bitter, tingle. |
| N-Cyclopropyl E2, Z6-dodecadienamide | Fatty mouthfeel, tongue burn, Wasabi like |
| N-Cyclopropyl E2, Z6-nonadienamide | Oily, tingle, strong MSG/umami mouthfeel. |
| N-Ethyl E2, Z6-dodecadienamide | Burn, MSG effect, oily flavor, green celery, sweet heating. |
| N-Ethyl E2, Z6-nonadienamide | Umami character |
| N-Isobutyl E2, Z6-dodecadienamide | Some tingle, anesthetic, numbing effect, interesting cooling/tingle effect, long lasting. The aftertaste is cooling and refreshing. |
| N-Isobutyl E2, Z6-nonadienamide | Strong tingle very long lasting, mint, oily, fizzy, tongue numbing, some MSG effect. |
| N-Isopropyl E2, Z6-dodecadienamide | Oily flavor, slight tingle. |
| N-Isopropyl E2, Z6-nonadienamide | Oily, cucumber, some tingle, bitter. |
| N-Methyl E2, Z6-nonadienamide | Warming, tingle |

The literature has not previously reported alkyldienamides having umami flavor. In addition, closely structurally related compounds such as dienals and unsaturated acids, are not specifically reported to possess umami character when tasted in isolation.

As used herein olfactory effective amount is understood to mean the amount of compound in flavor compositions the individual component will contribute to its particular olfactory characteristics, but the flavor, taste and aroma effect on the overall composition will be the sum of the effects of each of the flavor ingredients. As used herein taste effects include salt and umami, effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of alkyldienamides used in products is greater than 50 parts per billion, generally provided at a level of from about 50 parts per billion to about 800 parts per million in the finished product, more preferably from about 10 parts per million to about 500 parts per million by weight.

The usage level of alkyldienamides varies depending on the product in which the alkyldienamides are employed. For examples, alcoholic beverages the usage level is from about 1 to about 50 parts per million, preferably from about 5 to about 30 and most preferably from about 10 to about 25 parts per million by weight. Non-alcoholic beverages are flavored at levels of from about 50 parts per billion to about 5 parts per million, preferably from about 200 parts per billion to about 1 part per million and in highly preferred situations of from about 300 to about 800 parts per billion. Snack foods can be advantageously flavored using alkyldienamides of the present invention at levels of from about 10 to about 250 parts per million, preferably from about 50 to about 200 and most preferably from about 75 to about 150 parts per million by weight.

Toothpaste can be satisfactorily flavored by using alkyldienamides at levels of from about 150 to about 500 parts per million, more preferably from about 200 to about 400 parts per million by weight.

Candy products including hard candy can be flavored at levels of from about 10 to about 200; preferably from about 25 to about 150 and more preferably from 50 to 100 parts per million by weight. Gum usage levels are from about 300 to about 800, preferably from about 450 to about 600 parts per million.

The term "foodstuff" as used herein includes both solid and liquid ingestible materials for man or animals, which materials usually do, but need not, have nutritional value.

Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the alkyldienamides compounds of this invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the alkyldienamides of our invention; (2) that they be organoleptically compatible with the alkyldienamides derivative(s) of our invention whereby the flavor of the ultimate consumable material to which the alkyldienamides are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, other than the alkyldienamides of our invention and aldehydes; lactones; other cyclic organic materials including benzene derivatives, acyclic compounds, heterocyclies such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillin, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxy-phenol; amyl acetate; amyl cinnamate; γ-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2-propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propylpropenyl disulfide; propylpropenyl trisulfide; diallyl disulfide; diallyl trisulfide; dipropenyl disulfide; dipropenyl trisulfide; 4-methyl-2-[(methylthio)-ethyl]-1,3-dithiolane; 4,5-dimethyl-2-(methylthiomethyl)-1,3-dithiolane; and 4-methyl-2-(methylthiomethyl)-1,3-dithiolane. These and other flavor ingredients are provided in U.S. Pat. Nos. 6,110,520 and 6,333,180 hereby incorporated by reference.

The alkyldienamides derivative(s) of our invention or compositions incorporating them, as mentioned above, can be combined with one or more vehicles or carriers for adding them to the particular product. Vehicles can be edible or otherwise suitable materials such as ethyl alcohol, propylene glycol, water and the like, as described supra. Carriers include materials such as gum arabic, carrageenan, xanthan gum, guar gum and the like.

Alkyldienamides prepared according to our invention can be incorporated with the carriers by conventional means such as spray-drying, extrusion, drum-drying and the like. Such carriers can also include materials for coacervating the alkyldienamides of our invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of alkyldienamides utilized should be sufficient to impart the desired flavor characteristic to the product, but on the other hand, the use of an excessive amount of alkyldienamides is not only wasteful and uneconomical, but in some instances, too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the pre-consumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

With reference to the novel compounds of our invention, the synthesis is effected by means of the reaction of Z4-aldehydes with malonic acid under pyridine catalysis to furnish the known E2,Z6-acids. Subsequent reaction with ethyl chloroformate in the presence of triethylamine and further reaction of the intermediate with amine (added either directly or in solution) according to the scheme:

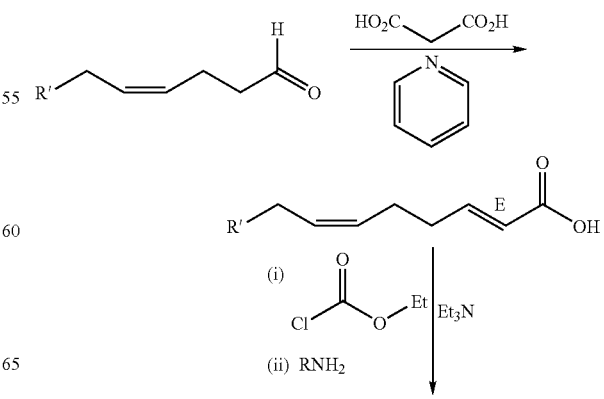

-continued

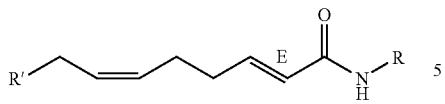

as set forth in examples herein. The acid is dissolved in dichloromethane to which ethylchloroformate is added in 1.0 to 2.0 equivalents at temperatures ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour.

The mixture is filtered, and the filtrate cooled to 0° C. The amine is added in 1.0 to 7.0 equivalents either neat or as a solution in THF and the reaction is aged for about 1-3 hours at room temperature.

The reaction can be quenched with aqueous sodium chloride, hydrogen chloride or sodium hydroxide depending of the need to remove residual acid or amine. The mixture is extracted into ethereal solvent or dichloromethane, washed to neutrality and solvent removed.

The crude product is purified by distillation or recrystallization depending on the physical properties.

The reaction occurs in 35-75% mole yield based on E2,Z6-acid.

The alkyldienamides of the present invention can be admixed with other flavoring agents and incorporated into foodstuffs and other products using techniques well known to those with ordinary skill in the art. Most commonly the alkyldienamides are simply admixed using the desired ingredients within the proportions stated.

The following are provided as specific embodiments of the present invention. Other modifications of this invention will be readily apparent to those skilled in the art, without departing from the scope of this invention. As used herein, both specification and following examples all percentages are weight percent unless noted to the contrary.

EXAMPLE 1

Preparation of Materials of the Present Invention

The following reaction sequence was used to prepare the specific compounds described by the NMR data set forth below:

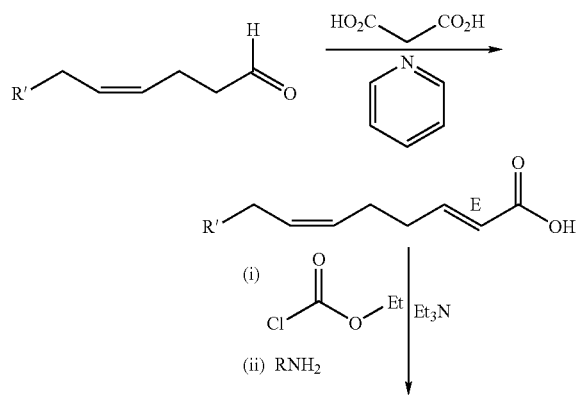

-continued

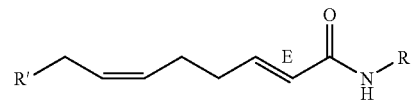

The acid is dissolved in dichloromethane to which ethylchloroformate is added in 1.0 to 2.0 equivalents at temperatures ranging from 0° C. to room temperature, most preferably from 10° C. to 20° C. The resulting solution is cooled to −10° C. to −30° C., and triethylamine is added in 1.0 to 2.0 equivalents such that the temperature range is below 0° C. and the mixture aged for 1 hour.

The mixture is filtered, and the filtrate cooled to 0° C. The amine is added in 1.0 to 7.0 equivalents either neat or as a solution in THF and the reaction is aged for 1-3 hours at room temperature.

The reaction can be quenched with aqueous sodium chloride, hydrogen chloride or sodium hydroxide depending on the need to remove residual acid or amine. The mixture is extracted into ethereal solvent or dichloromethane, washed to neutrality and solvent removed.

The crude product is purified by distillation or recrystallization depending on the physical properties.

The amides are synthesized according to the general scheme above with the following specific examples. Equivalents set out are mole equivalents based on starting acid, yields are distilled chemical yields based on starting acid.

N-methyl 2E,6Z-nonadienamide 2E,6Z-nonadienoic acid 1 eq, ethyl chloroformate 1.5 eq, triethylamine 1.5 eq, methylamine 1.5 eq as a 2.0M solution in THF, quench with 10% sodium chloride solution, yield=47%. 0.95 ppm (t, 3H, J=7.54 Hz, a), 2.02 ppm (quintet, 2H, J=7.33 Hz), 2.19 ppm (m, 4H, c), 2.78 & 2.85 ppm (d, 3H, J=4.81 & 4.87 Hz), 5.27-5.43 ppm (m, 2H, e), 5.90 ppm (d, 1H, J=15.36 Hz), 6.80 ppm (d, 1H, J=15.33 Hz, of t, J=6.59 Hz, g), 6.80 ppm (m, 1H).

N-ethyl 2E,6Z-nonadienamide 2E,6Z-nonadienoic acid 1 eq, ethyl chloroformate 1.5 eq, triethylamine 1.5 eq, ethylamine 7.0 eq as a 2.0M solution in THF, quench with 10% hydrogen chloride solution, yield=60%. 0.95 ppm (t, 3H, J=7.55 Hz), 1.16 ppm (t, 3H, J=7.27 Hz), 2.03 ppm (quintet, 2H, J=7.31 Hz), 2.20 ppm (m, 4H), 3.35 ppm (quintet, 2H, J=7.04 Hz), 5.27-5.44 ppm (m, 2H), 5.84 ppm (d, 1H, J=15.32 Hz), 6.16 ppm (br. s, 1H), 6.82 ppm (d, 1H, J=15.28 Hz, of t, J=6.51 Hz).

N-ethyl 2E,6Z-dodecadienamide 2E,6Z-dodecadienoic acid 1 eq, ethyl chloroformate 1.5 eq, triethylamine 1.5 eq, ethylamine 7.0 eq as a 2.0M solution in THF, quench with 10% hydrogen chloride solution, yield 65%. 0.89 ppm (t, 3H, J=6.86 Hz), 1.16 ppm (t, 3H, J=7.27 Hz), 1.29 ppm (m, 6H), 2.01 ppm (q, 2H, J=6.79 Hz), 2.20 ppm (m, 4H), 3.35 ppm (m, 2H), 5.30-5.44 ppm (m, 2H), 5.80 ppm (d, 1H, J=15.32 Hz), 5.87 ppm (br. s, 1H), 6.82 ppm (d, 1H, J=15.29 Hz, J=6.61 Hz).

N-isopropyl 2E,6Z-nonadienamide 2E,6Z-nonadienoic acid 1 eq, ethyl chloroformate 1.5 eq, triethylamine 1.5 eq, isopropylamine 3.0 eq, quench with 20% sodium chloride, yield=57%. 0.95 ppm (t, 3H, J=7.53 Hz), 1.17 ppm (d, 6H, J=6.59 Hz), 2.03 ppm (quintet, 2H, J=7.36 Hz), 2.19 ppm (m, 4H), 4.14 ppm (m, 1H), 5.27-5.44 ppm (m, 2H), 5.83 ppm (d, 1H, J=15.30 Hz), 5.99 ppm (br. s, 1H), 6.81 ppm (d, 1H, J=15.27 Hz, J=6.64 Hz).

N-isopropyl 2E,6Z-dodecadienamide 2E,6Z-dodecadienoic acid 1 eq, ethyl chloroformate 1.5 eq, triethylamine 1.5 eq, isopropylamine 3.0 eq, quench with 20% sodium chloride, yield=52%. 0.88 ppm (t, 3H, J=7.53 Hz), 1.18 ppm (d, 6H, J=6.59 Hz), 1.29 ppm (m, 6H), 2.02 ppm (q, 2H, J=7.36 Hz), 2.20 ppm (m, 4H), 4.14 ppm (m, 1H), 5.27-5.44 ppm (m, 2H), 5.62 ppm (br. s, 1 H), 5.78 ppm (d, 1H, J=15.30 Hz), 6.79 ppm (d, 1H, J=15.27 Hz, of t, J=6.64 Hz).

N-isobutyl 2E,6Z-nonadienamide 2E,6Z-nonadienoic acid 1 eq, ethyl chloroformate 1.2 eq, triethylamine 1.5 eq, isobutylamine 1.0 eq, quench with 10% sodium hydroxide, yield=33%. 0.92 ppm (d, 6H, J=6.74 Hz), 0.95 ppm (t, 3H, J=7.51 Hz), 1.80 ppm (septet, 1H, J=6.73 Hz), 2.03 ppm (quintet, 2H, J=7.27 Hz), 2.20 ppm (m, 4H), 3.14 ppm (t, 2H, J=6.53 Hz), 5.28-5.47 ppm (m, 2H), 5.85 ppm (d, 1H, J=15.29 Hz), 5.88 ppm (br. s, 1H), 6.82 ppm (d, 1H, J=15.27 Hz, of t, J=6.61 Hz,).

N-isobutyl 2E,6Z-dodecadienamide 2E,6Z-dodecadienoic acid 1 eq, ethyl chloroformate 1.2 eq, triethylamine 1.5 eq, isobutylamine 3.0 eq, quench with 10% hydrogen chloride solution, yield=41%. 0.88 ppm (t, 3H, J=6.99 Hz), 0.92 ppm (d, 6H, J=6.70 Hz), 1.29 ppm (m, 6H), 1.80 ppm (m, 1H, J=6.73 Hz), 2.01 ppm (q, 2H, J=6.75 Hz), 2.20 ppm (m, 4H), 3.14 ppm (t, 2H, J=6.47 Hz), 5.30-5.44 ppm (m, 2H), 5.84 ppm (d, 1H, J=15.30 Hz), 5.97 ppm (m, 1H), 6.82 ppm (d, 1H, J=15.28 Hz, of t, J=6.55 Hz).

N-(2-methylbutyl) 2E,6Z-nonadienamide 2E,6Z-nonadienoic acid 1 eq, ethyl chloroformate 1.5 eq, triethylamine 1.5 eq, 2-methylbutylamine 3.0 eq, quench with 20% sodium chloride, yield=37%. 0.90 ppm (d, 3H, J=6.57 Hz,), 0.90 ppm (t, 3H, J=7.45 Hz), 0.96 ppm (t, 3H, J=7.55 Hz.), 1.17 ppm (m, 1H), 1.42 ppm (m, 1H), 1.58 ppm (m, 1H), 2.03 ppm (quintet, 2H, J=7.33 Hz), 2.20 ppm (m, 4H), 3.09-3.29 ppm (m, 2H), 5.28-5.44 ppm (m, 2H), 5.80 ppm (br. s, 1H), 5.82 ppm (d, 1H, J=15.34 Hz), 6.82 ppm (d, 1H, J=15.23 Hz, of t, J=6.55 Hz).

N-(2-methylbutyl) 2E,6Z-dodecadienamide 2E,6Z-dodecadienoic acid 1 eq, ethyl chloroformate 1.5 eq, triethylamine 1.5 eq, 2-methylbutylamine 3.0 eq, quench with 20% sodium chloride, yield=45%. 0.7-0.92 ppm (m, 9H), 1.17 ppm (m, 1H), 1.29 ppm (m, 6H), 1.36 ppm (m, 1H), 1.57 ppm (m, 1H), 2.01 ppm (q, 2H, J=6.82 Hz), 2.20 ppm (m, 4H), 3.09-3.29 ppm (m, 2H), 5.30-5.44 ppm (m, 2H), 5.82 ppm (br. s, 1H), 5.83 ppm (d, 1H, J=15.27 Hz), 6.82 ppm (d, 1H, J=15.26 Hz, of t, J=6.58 Hz).

N-cyclopropyl 2E,6Z-nonadienamide 2E,6Z-nonadienoic acid 1 eq, ethyl chloroformate 1.5 eq, triethylamine 1.5 eq, cyclopropylamine 2.0 eq, quench with 10% hydrogen chloride solution, yield=49%. 0.53 ppm (m, 2H), 0.77 ppm (m, 2H), 0.95 ppm (t, 3H, J=7.53 Hz), 2.02 ppm (quintet, 2H, J=7.37 Hz), 2.19 ppm (m, 4H), 2.77 ppm (m, 1H), 5.26-5.43 ppm (m, 2H), 5.79 ppm (d, 1H, J=15.30 Hz), 6.15 ppm (br. s, 1H), 6.82 ppm (d, 1H, J=15.30 Hz, of t, J=6.58 Hz).

N-cyclopropyl 2E,6Z-dodecidienamide 2E,6Z-dodecadienoic acid 1 eq, ethyl chloroformate 1.5 eq, triethylamine 1.5 eq, cyclopropylamine 2.4 eq, quench with 10% hydrogen chloride solution, yield=55%. 0.53 ppm (m, 2H), 0.76 ppm (m, 2H), 0.88 ppm (t, 3H, J=6.85 Hz), 1.29 ppm (m, 6H), 2.00 ppm (q, 2H, J=6.80 Hz), 2.18 ppm (m, 4H), 2.78 ppm (m, 1H), 5.29-5.43 ppm (m, 2H), 5.83 ppm (d, 1H, J=15.34 Hz), 6.46 ppm (br. s, 1H), 6.82 ppm (d, 1H, J=15.30 Hz, of t, J=6.52 Hz).

N-(2-hydroxyethyl) 2E,6Z-dodecadienamide 2E,6Z-dodecadienoic acid 1 eq, ethyl chloroformate 1.5eq, triethylamine 1.5 eq, 2-ethanolamine 3.0 eq, quench with 20% sodium chloride and washed with dilute hydrogen chloride solution, yield=48%. 0.89 ppm (t, 3H, J=7.05 Hz), 1.29 ppm (m, 6H), 2.01 ppm (q, 2H, J=7.01 Hz), 2.20 ppm (m, 4H), 3.47 ppm (m, 2H), 3.73 ppm (m, 2H), 4.17-4.28 ppm (br. m, 1H), 5.29-5.44 ppm (m, 2H), 5.84 ppm (d, 1H, J=15.37 Hz), 6.43-6.47 ppm (br. m, 1H), 6.84 ppm (d, 1H, J=15.31 Hz, of t, J=6.54 Hz).

N-(3,4-methylenedioxy)benzyl 2E,6Z-nonadienamide 2E,6Z-nonadienoic acid 1 eq, ethyl chloroformate 1.5 eq, triethylamine 1.5eq, piperonylamine 1.5 eq, quench with 10% sodium hydroxide solution, re-crystallized from hexane, yield 72%. 0.95 ppm (t, 3H, J=7.53 Hz), 2.03 ppm (quintet, 2H, J=7.37 Hz), 2.20 ppm (m, 4H), 4.39 ppm (d, 2H, J=5.76 Hz), 5.27-5.44 ppm (m, 2H), 5.76 ppm (br. s, 1H), 5.78 ppm (d, 1H, J=15.38 Hz), 5.94 ppm (s, 2H), 6.75-6.79 ppm (m, 3H), 6.86 ppm (d, 1H, J=15.27 Hz, of t, J=6.59 Hz).

EXAMPLE 2

Preparation of Non-Alcoholic Beverage Flavor System

A non-alcoholic beverage formulation was prepared according to the following formulation.

| | |
|---|---|
| Water | 866.82 grams |
| High Fructose Corn Syrup 55 (77° Brix) | 129.8 grams |
| Citric Acid | 3.38 grams |

The flavor applied to the beverages consisted of a blend of single fold lemon oil and distilled lime oil. The control beverage contained 35 PPM of this flavor. This control beverage exhibited the taste characteristics of a tart lemon lime flavor. Another beverage was prepared containing 35 PPM of the same flavor and 0.5 PPM of N-Ethyl E2,Z6- nonadienamide. This beverage exhibited enhanced flavor impact, increased tartness, and an increased perception of freshness as well as it being described as having a more "natural" flavor.

EXAMPLE 3

Preparation of an Alcoholic Beverage Flavor System

Flavored beverages were prepared using the following 30° Proof alcoholic base:

| | |
|---|---|
| 190° Proof food grade Ethyl Alcohol | 157.89 milliliters |
| High Fructose Corn Syrup 55 (77° Brix) | 217.00 milliliters |
| Citric Acid (50% solution) | 3.00 milliliters |
| Water | 622.11 milliliters |

The peach flavor applied to the beverages consisted of a blend of Gamma Decalactone, Benzaldehyde, Cis-3-hexenol, Butyric acid, 2-Methyl butyric acid, Isobutyl acetate, Linalool, and para-Mentha-8-thiol-3-one. The control beverage contained 60 PPM of the above flavor blend. This control beverage exhibited the taste characteristics of a mild candied green peach. Another beverage was prepared containing 60 PPM of the same flavor and 20 PPM of N-(3,4-methylenedioxy)benzyl E2,Z6-nonadienamide. This beverage exhibited an enhanced perception of alcohol, increased flavor impact, and a tingle effect on the tongue.

EXAMPLE 4

Preparation of a Toothpaste Product

The following separate groups of ingredients were prepared:

Group "A"

| Ingredients | Weight Percent |
|---|---|
| glycerin | 30.2 |
| distilled water | 15.3 |
| sodium benzoate | 0.1 |
| sodium saccharin | 0.2 |
| stannous flouride | 0.5 |

Group "B"

| Ingredients | Weight Percent |
|---|---|
| calcium carbonate | 12.5 |
| dicalcium phosphate (dihydrate) | 37.2 |

Group "C"
2.0 parts by weight of sodium n-Lauroyl sarcosinate (foaming agent)

Group "D"
1.0 parts by weight of the flavor material which is a blend of peppermint oil, spearmint oil, anethole, and menthol.

Procedure:
(1) The ingredients in Group "A" were stirred and heated in a steam jacketed kettle to 160° F.
(2) Stirring was continued for an additional 3 to 5 minutes to form a homogeneous gel.
(3) The powders of Group "B" were added to the gel, while mixing until a homogeneous paste is formed.
(4) With stirring, the flavor of Group "D" was added, followed by addition immediately thereafter of the foaming agent of Group "C".
(5) The resultant slurry was then blended for one hour.

The completed paste was then transferred to a three-roller mill, homogenized and finally tubed. The resulting toothpaste when used in a normal tooth brushing procedure yields a slightly bitter/medicinal mint flavor which exhibits moderate cooling. To this control paste 200 ppm of N-Isobutyl E2,Z6-dodecadienamide is added. This toothpaste exhibits moderate cooling without the bitterness of the control sample. In addition the sample exhibits tingle on the tongue and a slight numbing on the lips.

EXAMPLE 5

Preparation of a Chewing Gum Flavor 100 parts by weight of vehicle were mixed with 5 parts by weight of bubble gum flavor which is a blend of orange oil, amyl acetate, clove bud oil, ethyl butyrate, and methyl salicylate. To this 300 parts sucrose and 100 parts corn syrup were added. Mixing was effected in a ribbon blender with jacketed sidewalls of the type manufactured by Baker Perkins Co. The resultant chewing gum blend was then manufactured into strips 1 inch in width and 0.1 inches in thickness. These strips were cut into lengths of 3 inches each. This control gum exhibited a fruity citrus spice flavor when chewed. Another gum sample was prepared using the above recipe with the addition of 0.25 parts of N-Isobutyl E2,Z6-nonadienamide. The resulting gum had a similar taste profile to the control gum, however, it exhibited a pleasant tingle effect when chewed.

EXAMPLE 6

Preparation of Flavor for use in Hard Candy

| | |
|---|---|
| Sugar | 137 grams |
| Corn Syrup 42 DE | 91 grams |
| Water | 46 grams |

The above ingredients were added to a stainless steel pot. With constant mixing the ingredients were brought to 295° F. The pot was removed from the heat and 0.5 grams of cinnamon bark oil was blended in. This liquid candy was then deposited into molds where it was left to cool. This recipe yielded 200 grams of finished candy. The resulting control candy exhibited a cinnamon bark type flavor with low to moderate warmth. Another candy sample was prepared using the above recipe with the addition of 100 PPM of N-Methyl E2,Z6-nonadienamide. This candy exhibited a greener flavor with less warmth, a slight numbing and a moderate level of tingle.

What is claimed is:

1. A process for augmenting, enhancing or imparting a taste or somatosensory effect to a foodstuff, comprising the step of adding to the foodstuff a taste or sensation augmenting, enhancing or imparting level of N-Cyclopropyl E2,Z6-nonadienamide.

2. The method of claim 1, wherein the level of N-Cyclopropyl E2,Z6-nonadienamide is from about 50 parts per billion to about 800 parts per million by weight.

3. A compound defined N-Cyclopropyl E2,Z6-nonadienamide.

4. A combination of a foodstuff and an organoleptically acceptable level of N-Cyclopropyl E2,Z6-nonadienamide.

5. The combination of claim 4, wherein the organoleptically acceptable level is greater than about 50 parts per billion.

6. The combination of claim 4, wherein the organoleptically acceptable level is from about 50 parts per billion to about 800 parts per million.

* * * * *